United States Patent
O'Brien, II

(10) Patent No.: US 9,974,558 B2
(45) Date of Patent: *May 22, 2018

(54) SURGICAL INSTRUMENT WITH DISTAL BEARING ASSEMBLY

(71) Applicant: Medtronic Xomed, Inc., Jacksonville, FL (US)

(72) Inventor: Todd Shay O'Brien, II, Saint Johns, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 199 days.

This patent is subject to a terminal disclaimer.

(21) Appl. No.: 14/877,150

(22) Filed: Oct. 7, 2015

(65) Prior Publication Data
US 2016/0022301 A1  Jan. 28, 2016

Related U.S. Application Data

(63) Continuation of application No. 13/362,463, filed on Jan. 31, 2012, now Pat. No. 9,155,555.

(51) Int. Cl.
A61B 17/32 (2006.01)
A61B 17/16 (2006.01)
A61B 17/24 (2006.01)

(52) U.S. Cl.
CPC .... *A61B 17/32002* (2013.01); *A61B 17/1688* (2013.01); *A61B 17/24* (2013.01); *A61B 2217/007* (2013.01)

(58) Field of Classification Search
CPC ............ A61B 17/1637; A61B 17/1657; A61B 17/1659; A61B 17/320016; A61B 17/32002
See application file for complete search history.

(56) References Cited

U.S. PATENT DOCUMENTS

| | | |
|---|---|---|
| 3,528,645 A | 9/1970 | Harken |
| 3,841,335 A | 10/1974 | Tarsitano |
| 5,405,348 A | 4/1995 | Anspach, Jr. et al. |
| 8,556,922 B2 | 10/2013 | Tidwell et al. |
| 2002/0013594 A1 | 1/2002 | Dinger et al. |
| 2003/0055404 A1 | 3/2003 | Moutafis |
| 2005/0177168 A1 | 8/2005 | Brunnett et al. |
| 2009/0270894 A1 | 10/2009 | Rubin et al. |
| 2010/0234724 A1 | 9/2010 | Jacobsen et al. |

(Continued)

FOREIGN PATENT DOCUMENTS

| | | |
|---|---|---|
| CN | 101123918 | 2/2008 |
| CN | 101686835 | 3/2010 |

(Continued)

OTHER PUBLICATIONS

International Search Report and Written Opinion for related Int'l Appln No. PCT/US2013/022656 dated Apr. 23, 2013 (12 pgs).

*Primary Examiner* — Ashley Fishback
(74) *Attorney, Agent, or Firm* — Dicke, Billig & Czaja, PLLC

(57) ABSTRACT

A surgical cutting instrument comprises an outer tubular member having a proximal section, an intermediate section and a central lumen. An inner tubular member is rotatably received within the central lumen and includes a distal end forming a cutting member extending distally beyond, and exposed relative to, the distal section of the outer tubular member. A bearing assembly is coupled to the outer tubular member and the inner tubular member.

20 Claims, 7 Drawing Sheets

(56) References Cited

U.S. PATENT DOCUMENTS

| | | |
|---|---|---|
| 2010/0249786 A1 | 9/2010 | Schmieding et al. |
| 2011/0118660 A1 | 5/2011 | Torrance et al. |

FOREIGN PATENT DOCUMENTS

| | | |
|---|---|---|
| DE | 102008045179 | 3/2010 |
| EP | 0744160 | 11/1996 |
| EP | 1598023 | 11/2005 |
| WO | 0122890 | 4/2001 |
| WO | 0176680 A1 | 10/2001 |
| WO | 2008042987 | 4/2008 |

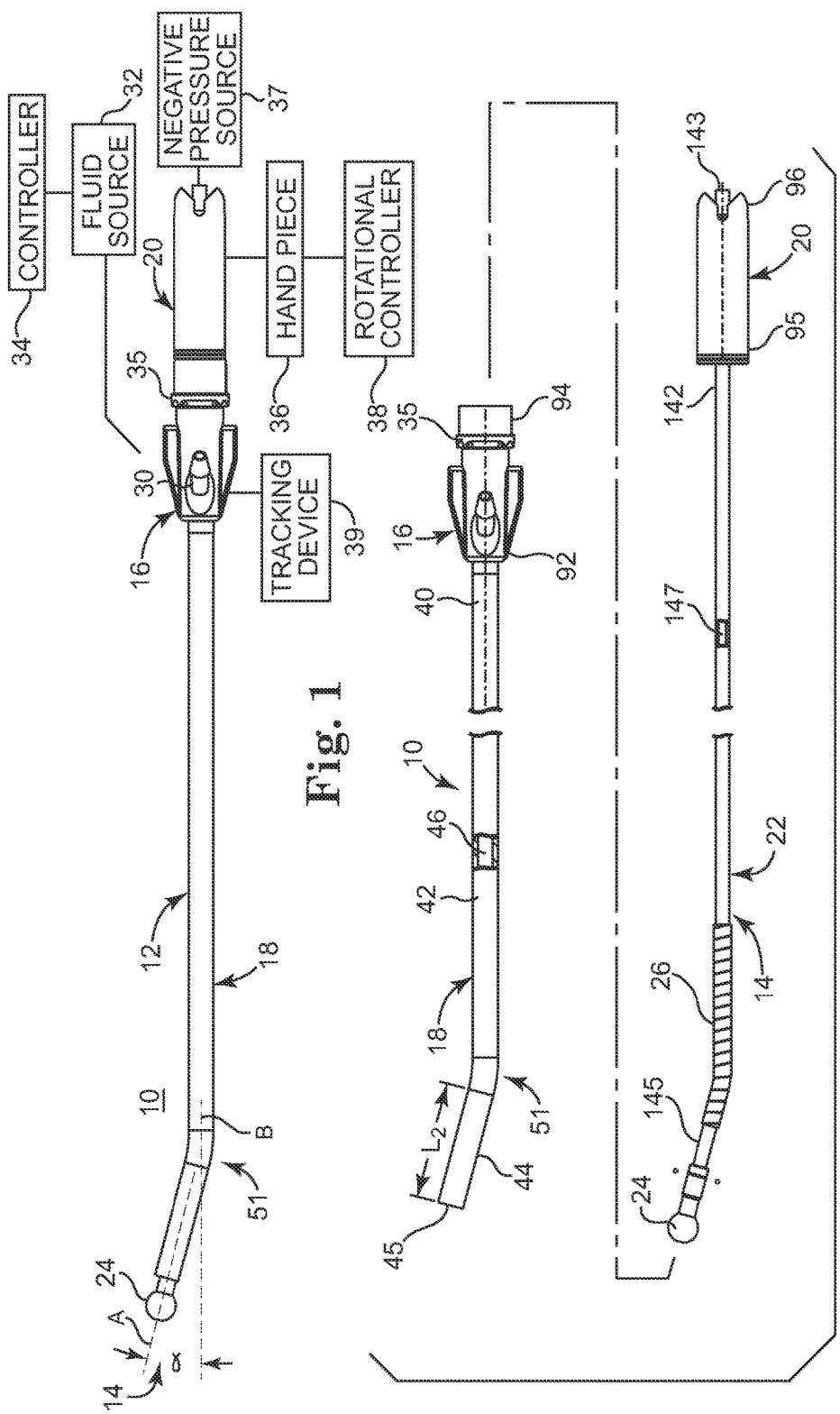

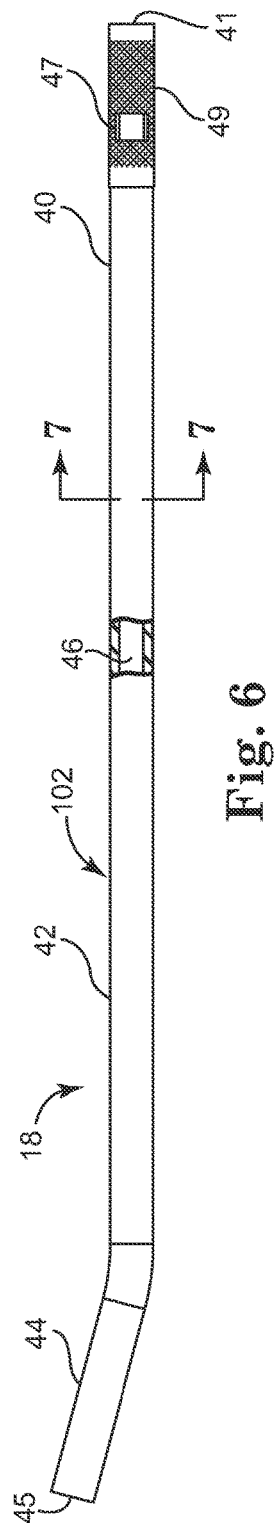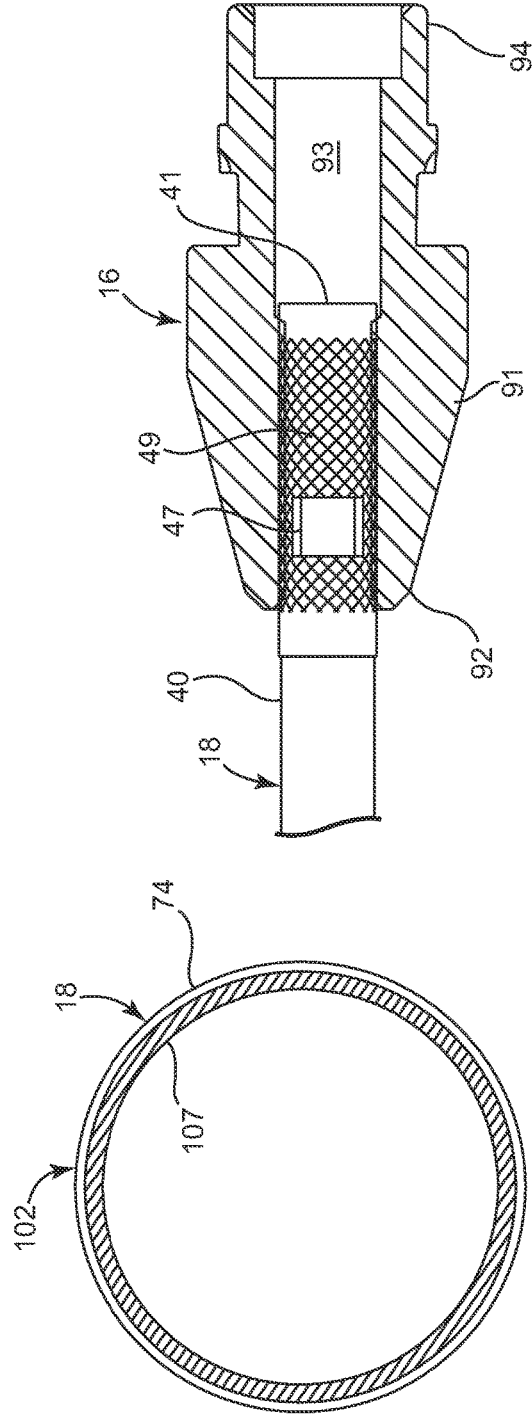

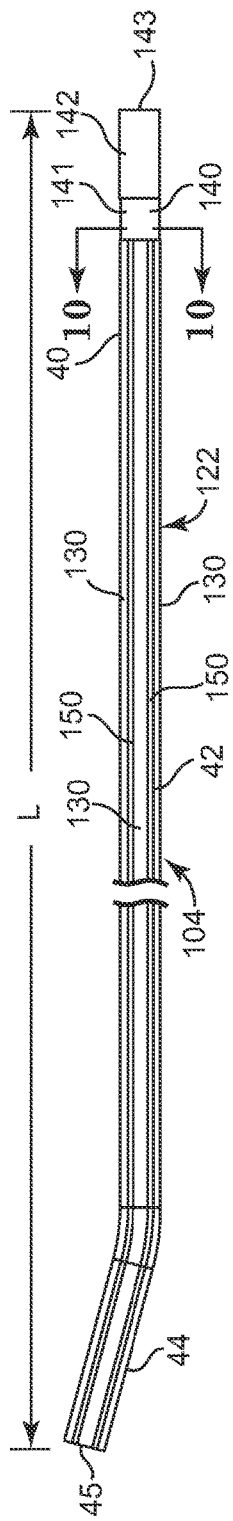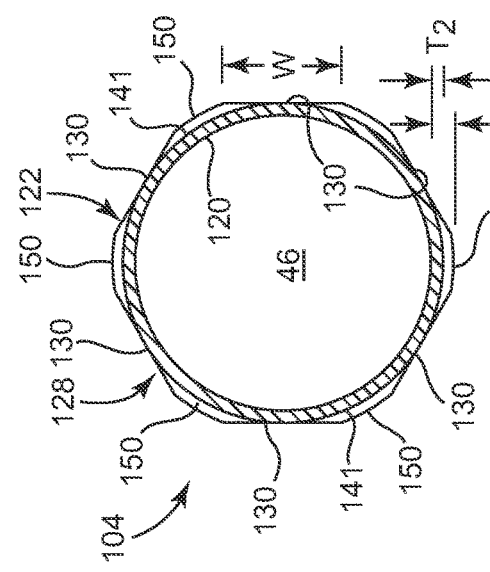

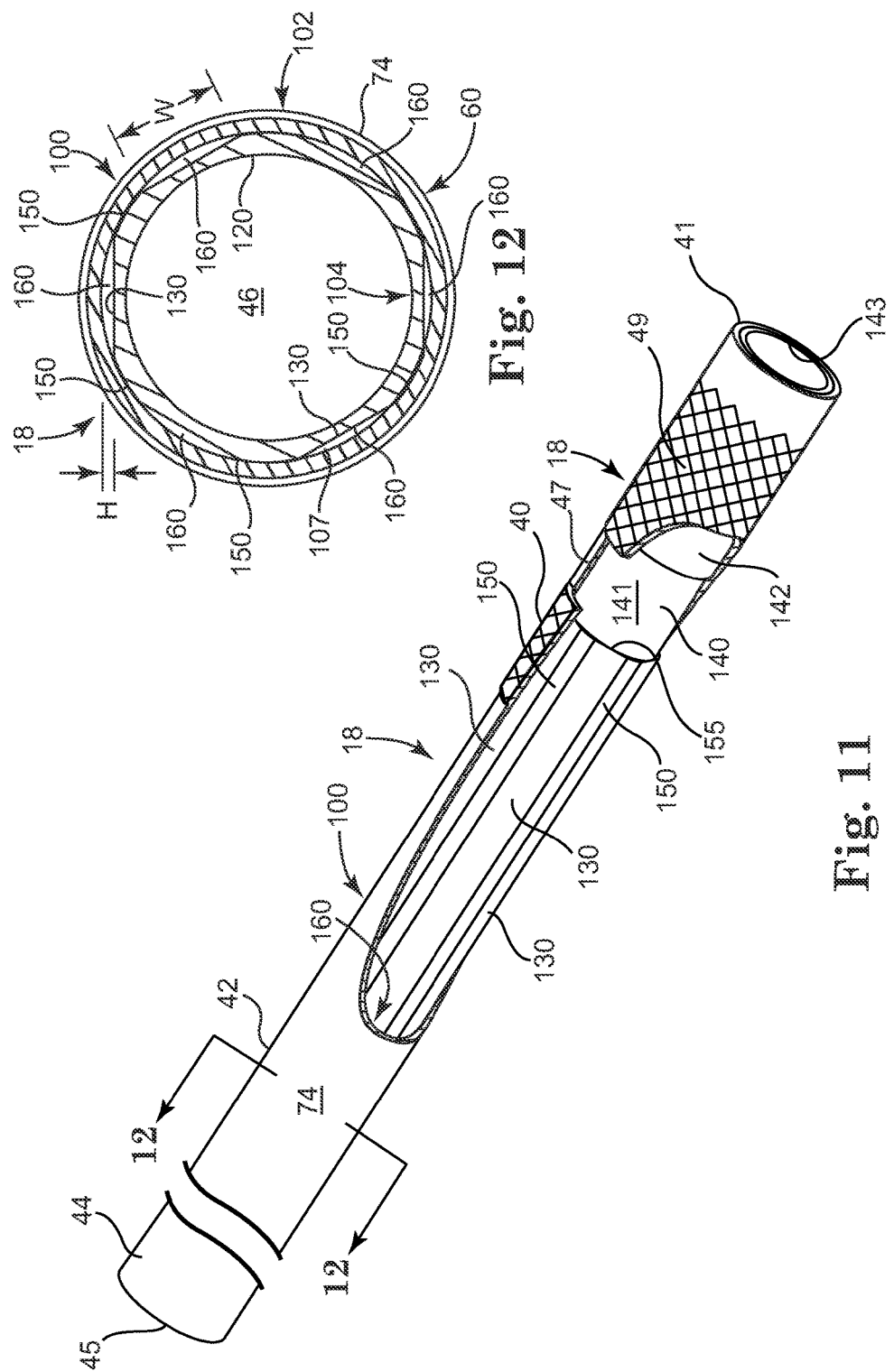

SURGICAL INSTRUMENT WITH DISTAL BEARING ASSEMBLY

CROSS-REFERENCE TO RELATED APPLICATION

This application is a continuation of U.S. patent application Ser. No. 13/362,463 filed on Jan. 31, 2012, and incorporated herein by reference.

BACKGROUND

Powered surgical instruments have been developed for use in many orthopedic ear-nose-throat (ENT) operations as well as other operations in and around the skull. One type of cutting instrument includes a bur supported by an inner tubular member that is rotatable with respect to an outer tubular member. The bur is used to debride a target tissue of a treatment site. In many instances, the bur and/or treatment site are irrigated to facilitate lubrication of the treatment site as well as to cool the bur. In other instances, aspiration is applied to the treatment site to remove debrided tissue as well as to remove excess fluid.

In some current cutting instruments, the inner tubular assembly can employ a spring section to impart flexibility into the instrument. While the added flexibility is gained, the corresponding bur coupled with the inner tubular member can experience significant axial movement with respect to the outer tubular member. This axial movement can add undesired stress to the inner tubular member. Additionally, the axial movement presents difficulty in tracking a location of the bur relative to a patient or positions within a patient anatomy, for example when employing instrument tracking and navigation technology. Accordingly, surgical instruments with a distal bur exhibiting axial movement can reduce the effectiveness of micro-debriding instruments by increasing stress on an inner tubular member and preventing accurate tracking of the instrument.

SUMMARY

A surgical cutting instrument comprises an outer tubular member having a proximal section, an intermediate section and a central lumen. An inner tubular member is rotatably received within the central lumen and includes a distal end forming a cutting member extending distally beyond, and exposed relative to, the distal section of the outer tubular member. A bearing assembly is coupled to the outer tubular member and the inner tubular member.

BRIEF DESCRIPTION OF THE DRAWINGS

FIG. 1 is perspective view of a system including a surgical debriding instrument, in accordance with principles of the present disclosure;

FIG. 2 is as assembly view of the instrument;

FIG. 6 is a top plan view of an outer portion of an outer tubular member of a debriding instrument;

FIG. 7 is a cross-sectional view of the instrument as taken along lines 7-7 of FIG. 6;

FIG. 8 is an enlarged partial cross-sectional view of a proximal portion of the instrument of FIG. 6 as secured within an outer hub;

FIG. 9 is a top plan view of an inner portion of the outer tubular member of the debriding instrument, FIG. 10 is a cross-sectional view of the instrument as taken along lines 10-10 of FIG. 9;

FIG. 11 is a perspective view of the outer tubular member illustrating the interior passages of the side wall of the outer tubular member; and FIG. 12 is a cross-sectional view of the outer tubular member as taken along lines 12-12 of FIG. 11.

DETAILED DESCRIPTION

Figure 3:
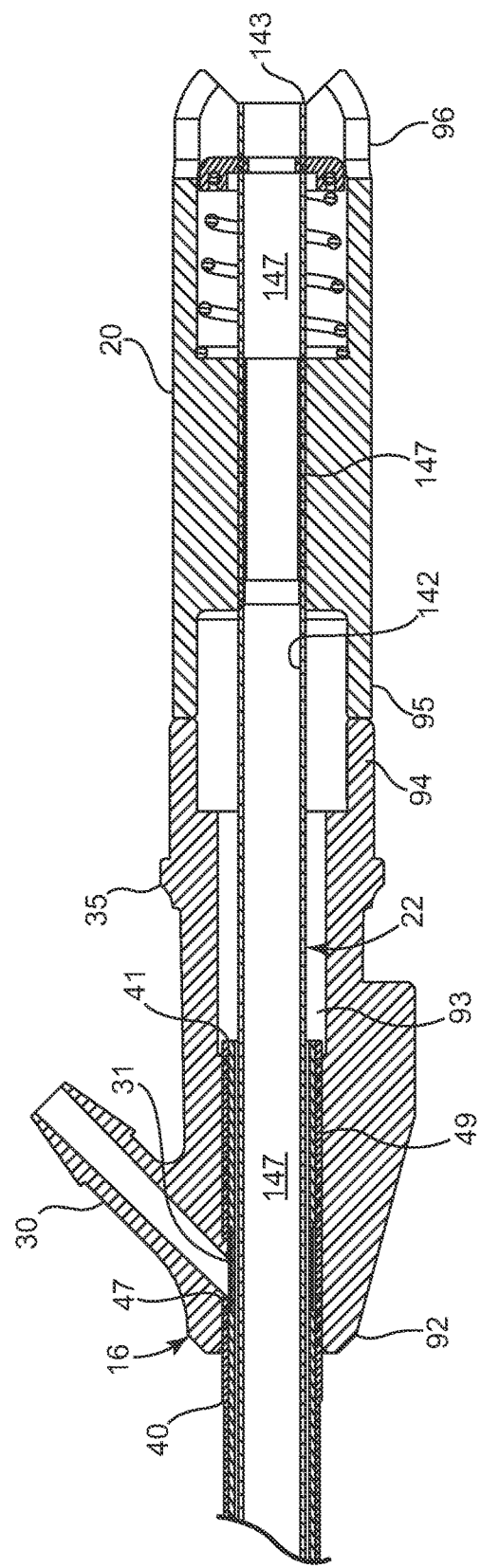
FIG. 3 is an enlarged partial cross-sectional view of the instrument of FIG. 2.

Embodiments of the present disclosure are directed to cutting instruments having a distal bearing assembly to inhibit axial movement of a distal cutting tip.

In one embodiment, the cutting instrument includes an inner tubular member rotatably received within an outer tubular member and which includes a cutting member such as a bur at its distal end. The inner tubular member and the outer tubular member each include a hub to facilitate their rotational relationship and their control by a handpiece that further supports both the inner tubular member and the outer tubular member. Rotation of the bur via rotation of inner tubular member causes debriding of the target tissue at a treatment site.

The outer tubular member includes a side wall defining an interior passage that acts as an irrigation pathway to supply an irrigation fluid to the treatment site adjacent to the bur. Because the irrigation pathway is incorporated internally and not provided through an external tube (as in conventional cutting instruments), the cutting instrument has a low cross-sectional profile. This smaller cross-sectional profile enables insertion of distal cutting end of the instrument into smaller treatment sites and facilitates introduction of the distal cutting end through narrow and/or curved passageways that provide access to the treatment site. In another aspect, by providing the irrigation pathway within a sidewall of the outer tubular member, interaction of the irrigation fluid with the inner tubular member (or other components internal to cutting instrument) is avoided.

A distal bearing assembly limits axial movement of the bur and inner tubular member relative to the outer tubular member. The distal bearing assembly, in some embodiments, employs one or more balls to couple the bur with the irrigation pathway. In one aspect, the balls are equally spaced about a circumference of the bur and positioned within apertures of the irrigation pathway and a race of the bur.

In some embodiments, the bur and the inner tubular member further define an aspiration pathway through an interior of the bur (and the inner tubular member) to avoid the conventional arrangement of an external aspiration tube of the types typically used in conventional instruments. In the embodiments, the inner tubular member has a length so that the aspiration pathway may extend continuously through a hub assembly of both the inner tubular member and the outer tubular member. Accordingly, with this arrangement, the internally incorporated aspiration pathway further maintains the low cross-sectional profile that is achieved via arranging the irrigation pathway within a side wall of the outer tubular member, as described above.

In one embodiment, the instrument can be configured to be utilized in an electromagnetic image guided system, wherein the instrument is equipped with at least one tracking device. One exemplary electromagnetic image guided system is disclosed in U.S. Patent App. Pub. No. 2010/0234724, filed on Mar. 10, 2009, entitled "Navigating A Surgical Instrument", the contents of which are hereby incorporated by reference in their entirety. In general, the tracking device can include one or more coils that can provide an indication of position and orientation of the device to the image guided system. This indication can be useful during a surgical procedure that utilizes the surgical instrument.

Surgical instruments embodying principles of the present disclosure can be employed in various types of surgery including, but not limited to, various sinus procedures, skull base tumor removal (such as pituitary tumors, clivus chordomas, etc.), mastoidectomy, temporal bone tumor removal, craniotomy, a modified Lothrop procedure, spinal diseases, notchplasty, acromioplasty, laminotomy, laminectomy and the like.

These and other embodiments are described more fully in association with FIGS. 1-12.

One preferred embodiment of a surgical micro-burring instrument 10 is illustrated in FIGS. 1-2. The instrument 10 includes an outer tubular assembly 12 and an inner tubular assembly 14 (referenced generally in FIG. 1). With particular reference to FIG. 2, the outer tubular assembly 12 includes an outer hub 16 and an outer tubular member 18, whereas the inner tubular assembly 14 includes an inner hub 20 and an inner tubular member 22. The inner tubular member 22 is sized to be coaxially received within the outer tubular member 18 and forms a cutting member embodied as a bur 24. Other example cutting members can include various blades and the like configured to cut tissue. The inner tubular member 22 includes a proximal section 142 with end 143 and a distal section 145. Inner tubular member 22 additionally comprises a spring section 26 positioned proximal to bur 24 at distal section 145. Spring section 26 imparts flexibility into the inner tubular member 22 such that the inner tubular member can assume a curvature of the outer tubular assembly 22. In one aspect, an inner surface of inner tubular member 22 defines a lumen 147.

As illustrated in FIG. 1, the outer tubular member 18 extends distally from the outer hub 16. To this end, the outer hub 16 can assume a wide variety of forms known in the art. In some embodiments, outer hub 16 comprises an irrigation port 30 configured for fluid communication via tubing (not shown) with a fluid source 32 controlled by controller 34.

As illustrated in FIG. 1 and with additional reference to FIG. 3, the inner tubular member 22 extends distally from inner hub 20. With continued reference to FIG. 1, in some embodiments, inner hub 20 extends from a distal end 95 to a proximal end 96 and is configured to be engaged by a handpiece 36 for handling instrument 10. In particular, rotational controller 38 (via a connection between handpiece 36 and inner hub 20) enables selective rotational control over inner tubular member 22 to cause high-speed rotation of bur 24 for debriding or otherwise cutting a target tissue.

Additionally, inner tubular member 22 is optionally coupled to a negative pressure source 37 that provides suction to the bur 24. Moreover, hub 16 can be coupled with a suitable tracking device 39 such that instrument 10 can be used with a suitable electromagnetic image guided system that can determine a position of bur 24 within a patient's anatomy. In one embodiment, the tracking device 39 includes one or more magnetic coils detectable by the image guided system that can be used to display a representation of the instrument 10 and bur 24 with respect to a patient's anatomy. The magnetic coils can provide a reference location detectable by the image guided system such that, based on the reference location, an orientation and position of the bur 24 can be determined by the image guided system during a pre-operation procedure (e.g., utilizing a computed tomography (CT) or magnetic reasonable imaging (MRI) scan). During a surgical procedure, an indication of the orientation and position of bur 24 can be provided to assist a surgeon, for example by providing an image of the bur 24 on a monitor with respect to a patient's anatomy.

With reference to FIG. 2, the outer tubular member 18 is an elongated tubular body defining a proximal section 40 with proximal end 41 (FIG. 6), an intermediate section 42, a distal section 44 with distal end 45 (FIG. 6), and a central lumen 46. The outer tubular member defines a slight bend, as referenced generally by 51, at a junction between distal section 44 and proximal section 40 of the instrument 10. In one embodiment and further reference to FIG. 1, the bend 51 is configured to cause a central axis (as represented by dashed line A) of the distal section 44 to define an angle α in the range of 10°-90°, relative to a central axis (as represented by dashed line B) of the proximal section 40 of the instrument 10. Among other uses, this bend 51 is particularly useful in properly positioning the distal section 44 during a skull-based procedure, among other surgical procedures favoring bend 51 in distal section 44. To facilitate necessary rotation of the inner tubular assembly 14 in the region of the bend 51 (such as for rotating the bur 24 at a distal end thereof), the inner tubular member is preferably flexible and formed of an appropriate material employing spring section 26. In particular, the spring section 26 can assume a shape of the outer bend 51 due to flexibility of the spring section 26. Alternatively, other constructions can be employed. For example, bend 51 can be eliminated such that outer tubular member 18 is substantially straight.

The central lumen 46 extends from the proximal section 40 to the distal section 44. In this regard, and as described in greater detail below, the distal section 44 is open at a distal end 45 thereof to enable the inner tubular member 22 to extend distally beyond the distal end 45 of outer tubular member 18. Similarly, the proximal section 40 is open at a proximal end 41 thereof to facilitate positioning of the inner tubular member 22 within the central lumen 46. Moreover, with additional reference to FIGS. 3, 6, and 8, proximal section 40 comprises a proximal window 47 located distally of proximal end 41. In some embodiments, proximal section 40 additionally comprises a knurled portion 49 located on a surface of proximal section 40 and that surrounds the proximal window 47. In one aspect, knurled portion 49 facilitates securing proximal section 40 to an inner portion of outer hub 16, as illustrated in FIGS. 3 and 8.

In one suitable configuration, as illustrated in FIG. 8, the proximal portion 40 is inserted into a lumen 93 of outer hub 16 to secure knurled portion 49 within the distal section 92 and intermediate section 91 of outer hub 16. While better seen in FIG. 3, the proximal section 40 is advanced proximally within lumen 93 of outer hub 16 until window 47 is aligned underneath a bottom opening 31 of irrigation port 30, and then secured in this position to maintain fluid communication between irrigation port 30 and proximal window 47. In addition, in this configuration, proximal end 41 is open to lumen 93 of outer hub 16. Accordingly, in one aspect, the proximal section 40 has an outer diameter adapted to receive the outer hub 16 thereon.

However, the remainder of the outer tubular member 18 preferably provides a relatively uniform outer diameter (as represented by reference numeral 74 in FIG. 7) selected to perform the desired sinus procedure and a relatively uniform inner diameter (as represented by reference numeral 107 in FIG. 7) selected to rotatably receive the inner tubular member 22. For example, in one embodiment, the intermediate section 42, as well as the distal section 44, permit use of the inner tubular member 22/bur 24 as part of a sinus procedure.

Returning to FIG. 2, the inner tubular member 22 extends from the inner hub 20. In one preferred embodiment, the inner hub 20 is configured for selective attachment to handpiece 36 that can be operated to automatically rotate the inner tubular member 22 during use.

As previously described, the inner tubular member 22 forms bur 24 at a distal end thereof. In general terms, bur 24 is a solid member that can assume a variety of forms and is adapted with an abrasive or rough surface to cut or abrade bodily tissue upon rotation thereof. In some embodiments, the bur 24 forms a cutting surface including one or more cutting elements. While a spherical bur configuration is shown, it will be appreciated that other configurations can be used including, but not limited to, cylindrical, hemispherical, ellipsoidal, and pear-shaped configurations.

With reference to FIGS. 1-3, the micro-burring instrument 10 is assembled by coaxially positioning the inner tubular member 22 within the outer tubular member 18 via the central lumen 46. With particular reference to FIG. 3, the inner hub 20 (at distal end 95 of inner hub 20) abuts against the outer hub 16 (at proximal end 94 of inner hub 16). With this in mind, the inner tubular member 22 and inner hub 20 of inner assembly 14 is rotatable relative to the outer tubular member 18 and outer hub 16 of outer assembly 12. To this end, a distance of separation between the inner hub 20 and the bur 24 is greater than a distance of separation between the outer hub 16 and the distal end 45 of outer tubular member 18, thereby dictating that a desired position of the bur 24 will be exposed relative to the outer tubular member 18, as shown in FIG. 1. In particular, the inner tubular member 22 is coaxially disposed within the outer tubular member 18 such that the distal end 45 of the outer tubular member 18 is proximal to the bur 24 and to the distal end 145 of inner tubular member 22. Outer hub 16 can further define a shoulder 35 for engaging handpiece 36.

With further reference to FIGS. 4A-4D, instrument 10 further includes a distal bearing assembly 61 that limits axial movement of bur 24 relative to outer tubular member 18, and in particular limits axial movement of bur 24 in a direction parallel to central axis A (FIG. 1) of distal section 44. In the embodiment illustrated, bearing assembly 61 includes a plurality of balls 62 (three in the illustrated embodiment, two of which are shown) maintained within the outer tubular member 18 and coupled with the bur 24 through a circular race 63.

Balls 62, in one embodiment, are spherically shaped and formed of ceramic material equally spaced about the circular race 63 (i.e., spaced 120° from one another). In other embodiments, a fewer or greater number of balls than three can be used. The bur 24, and in particular race 63, can be formed of various materials, examples of which include, but are not limited to 440 stainless steel, M2 tool steel, carbide, etc. Thus, in one embodiment, balls 62 are formed of a first material (e.g., ceramic) and race 63 is formed of a second material (e.g., 440 stainless steel), different than the first material. In some instances, the use of different materials for balls 62 and race 63 can preclude galling and/or wear.

Regardless of the materials selected for balls 62 and race 63, bearing assembly 61 controls axial and radial position of bur 24 with respect to the tube 102, allowing for precise tracking of the bur 24 while utilized with an electromagnetic image guided system. Additionally, rolling contact between balls 62 and race 63 provides reduced friction when compared to sliding contact between bur 24 and inner portion 104. Thus, a temperature of the outer portion 102 during operation is reduced such that damage of tissue proximate and/or in contact with the outer portion 102 can be prevented. Moreover, a separate thrust bearing for instrument 10 is not needed. The bearing assembly 61 can operate and is similar in construction to a ball bearing, wherein inner portion 104 acts as a ball carrier for balls 62, bur 24 acting as an inner race. The outer portion 102 need not bear a load from balls 62 and can be provided so as to hold balls 62 in place within apertures 106. Upon final assembly, the bearing assembly 61 restricts axial motion of bur 24 while allowing rotation of the bur 24 relative to outer portion 102 and inner portion 104.

Figure 4A:
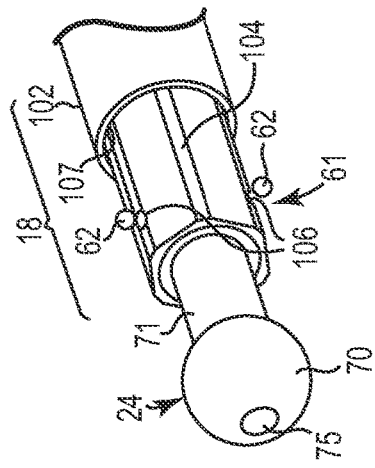
FIGS. 4A-4D are perspective views of a distal bearing assembly of a debriding instrument.
Figure 4B:
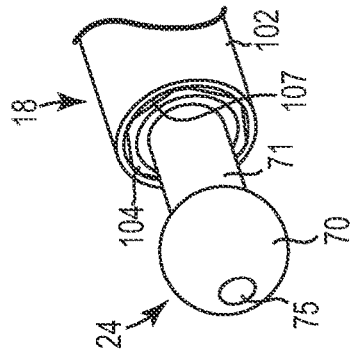
Figure 4C:
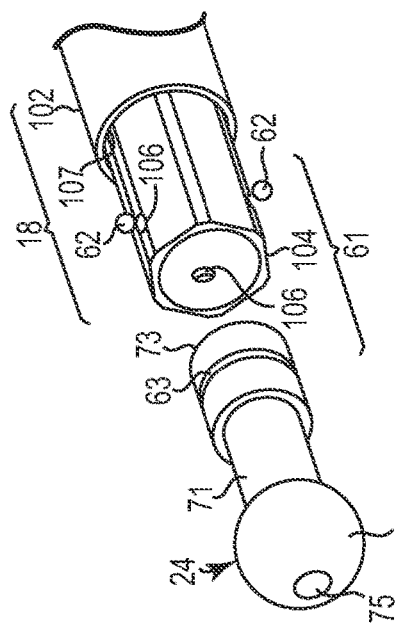
Figure 4D:
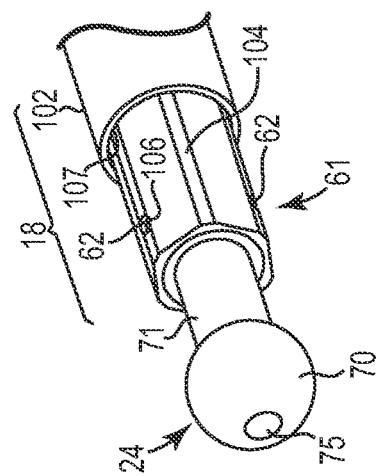

Bur 24 terminates at a tip 70 at one end, includes a shaft 71 and terminates at a proximal end 73 opposite the tip 70. Race 63 is machined into the bur 24 near the proximal end 73. Additionally, bur 24 includes an inner lumen 75 to deliver suction to tissue being cut by tip 70. As discussed in more detail below, outer tubular member 18 includes an outer portion 102 and an inner portion 104. The plurality of balls 62 are positioned within corresponding apertures 106 within the inner portion 104. When fully assembled as shown in FIG. 4D, the balls 62 engage the circular race 63 and are covered by the outer portion 102. Moreover, while tip 70 is shown as having a generally spherical shape in FIG. 4, bur 24 can take other forms, as previously described in association with FIGS. 1-2.

Figure 5:
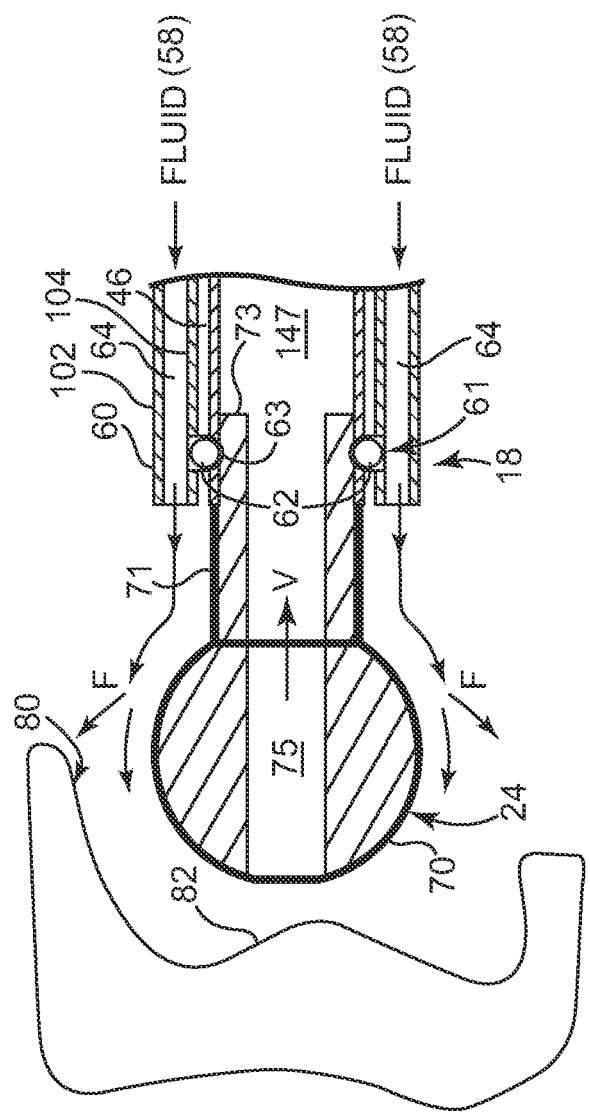
FIG. 5 is a schematic illustration of irrigating a treatment site using a debriding instrument.

As illustrated by FIGS. 1-2 and with additional reference to FIG. 5, once bur 24 is positioned at treatment site 80 to debride target tissue 82, fluid 58 supplied from fluid source 32 flows through an interior passage 64 (e.g., formed between outer portion 102 and inner portion 104) of side wall 60 of outer tubular member 18 to irrigate bur 24 and/or the treatment site 80. In one aspect, this arrangement enables flooding the treatment site 80 with fluid 58 (and as further represented by arrows F), as appropriate to the procedure, while the bur 24 is rotating to cut the target tissue 82. In some embodiments, the fluid 58 irrigates the treatment site 80 before and/or after the bur 24 rotates to cut the target tissue 82. While side wall 60 can take many forms, one particular embodiment is illustrated in FIGS. 7-12, as described in more detail hereafter.

Tip 70 of the bur 24 forms a lumen 75 that extends through shaft 71 of bur 24 and which is open to the central lumen 147 defined by inner tubular member 22. By forming lumen 75 to extend through bur 24, a smaller overall, cross-sectional profile of instrument 10 is maintained in accordance with the smaller cross-sectional profile achieved via providing an irrigation pathway within interior passage 64 of side wall 60 of outer tubular member 18. Regardless, the central lumen 147 serves as an aspiration conduit for the micro-burring instrument 10. Further, with reference to FIG. 5, when instrument 10 equipped with an aspiration pathway including central lumen 147 is applied to treat target site 82, the lumen 75 extending through bur 24 enables periodic or continuous aspiration (as represented by arrow V) via the central lumen 147 of the inner tubular member 22 to remove abraded tissue from the target site 82.

While outer tubular member 18 was previously described in association with FIGS. 1-2, outer tubular member 18 can take many forms to achieve the configuration of a side wall 60 that defines an interior passageway 64 configured to provide fluid to cool bur 24 and/or lubricate treatment site 80, as previously described in association with FIG. 5. Nevertheless, in one configuration, outer tubular member 18 comprises an assembly 100 formed from outer portion 102 shown in FIGS. 6-8 and inner portion 104, as shown in FIGS. 9-10. Outer portion 102 and inner portion 104 comprise two separate members that are joined together to produce assembly 100 having the form shown in FIGS. 11-12. For the sake of illustrative clarity, each of the inner portion 102 and the outer portion 104 will be further described separately.

FIG. 7 is a cross-sectional view of outer portion 102 of outer tubular member 18 and illustrates outer portion 102 defining a hollow sleeve. In one aspect, an outer surface of outer portion 102 of outer tubular member 18 comprises substantially the same features and attributes that were previously described in association with FIGS. 3, 6, and 8 for outer tubular member 18 as a whole. In one aspect, FIG. 7 further illustrates outer portion 102 including inner surface 107 that defines a diameter sized and adapted to receive inner portion 104. Outer portion 102 also defines outer surface 74 which forms the outer surface of outer tubular member 18 and which provides a generally uniform and generally smooth outer diameter.

FIG. 9 is a side plan view of inner portion 104 of outer tubular member 18 and FIG. 10 is a cross-sectional view of inner portion 104, according to principles of the present disclosure. While inner portion 104 can take many forms, in the one configuration shown in FIGS. 9-10, inner portion 104 defines an inner surface 120 and an outer surface 122. The inner surface 120 defines a generally uniform diameter and is generally uniformly smooth from the proximal section 40, through the intermediate section 42, to the distal section 44. However, the outer surface 122 defines an array 128 of elongate recesses 130 extending from the distal section 44, along intermediate section 42, and through at least a portion of proximal section 40. In one embodiment, the elongate recesses 130 extend along a majority of the length of inner portion 104 (and therefore a majority of a length of outer tubular member 18) before terminating adjacent a circular recess 140 that extends transversely to the elongate recesses 130. In one aspect, circular recess 140 forms a ring extending about a circumference of outer surface of inner portion 104. The circular recess 140 is in fluid communication simultaneously with each of the elongate recesses, as will be further illustrated later in FIG. 11.

As illustrated in FIG. 9, in one aspect, outer surface 122 of inner portion 104 further defines a non-recess portion 142 proximal to circular recess 140. This non-recess portion 142 is sized and adapted to be sealingly secured to an inner surface 107 of outer portion 102. In one embodiment, non-recess portion 142 is laser welded relative to inner surface 107 of outer portion 102. This arrangement secures the inner portion 104 to outer portion 102 at proximal section 40 of outer tubular member 18 (located proximal to proximal window 47 shown in FIGS. 6 and 8) while simultaneously defining a terminal end of the fluid communication pathway that extends generally within sidewall 60 of outer tubular member 18. Accordingly, fluid flowing into outer tubular member 18 at proximal section 40 (from port 30 and fluid source 32) will enter through proximal window 47 of outer tubular member 18, and flow through circular recess 130 (FIGS. 3, 6, and 8) just distal to non-recess portion 142 of inner portion 104 before proceeding into recesses 130.

As best seen in FIG. 10, the elongate recesses 130 of inner portion 104 (of outer tubular member 18) form an array 128 of recesses 130 uniformly spaced apart about the circumference of inner portion 104 with each elongate recess 130 being defined between an adjacent pair of raised protrusions 150 formed on outer surface 122 of inner portion 104. In the one configuration shown in FIG. 10, array 128 includes six elongate recesses 130 that are spaced apart uniformly (i.e., equidistant from each other) about the circumference of outer surface 122 of inner portion 104. Of course, in other configurations, there can be greater or fewer than six elongate recesses 130. Nevertheless, at least one recess 130 is provided to form interior passageway 64 in side wall 60 of outer tubular member 18. Configurations with a greater number of recesses (instead of fewer recesses) spaced apart uniformly about the circumference of the inner portion (and consequently about the circumference of the outer tubular member 18) provide more balance to the fluid flow through side wall 60. This arrangement enables outer tubular member 18 to have a smaller thickness of the side wall because each recess 130 can have a smaller thickness or height (as represented by H in FIG. 12) while enabling generally the same volume of fluid to flow within the side wall 60 of the outer tubular member 18.

While a variety of techniques may be used to form the inner portion 104, in one embodiment inner portion 104 is formed by providing a generally tubular sleeve (not shown) having a first thickness and then cutting an outer surface of the sleeve (corresponding to outer surface 122) to create each elongate recess 130. Accordingly, with reference to FIG. 10, the protrusions 150 generally define the original, first thickness (as represented by T1) of the sleeve while the recesses 130 extending between the respective protrusions 150 comprise a second thickness (as represented by T2) substantially less than the first thickness. The difference between the first thickness and the second thickness will then define a height of the recess 130, as best seen in FIG. 11. In one aspect, the height of each recess 130 (as represented by H, the difference between T1 and T2), the width of each recess 130 (as represented by W), and the number of recesses defines the cross-sectional area available to send fluid through the interior passageway 64 within the sidewall 60 of outer tubular member 18.

FIG. 11 is a perspective view of assembly 100 of outer tubular member 18 showing inner portion 104 and outer portion 102 in an assembled state to form outer tubular member 18. FIG. 12 is cross-sectional view of assembly 100 of FIG. 11 that further illustrates the relationship between inner portion 104 and outer portion 102 of assembly 100 of outer tubular member 18.

As seen in FIGS. 11-12, after slidably inserting inner portion 104 within outer portion 102, inner portion 104 becomes coaxially disposed within outer portion 102. With this arrangement, the protrusions 150 contact inner surface 107 of outer portion 102, thereby forming separate conduits 160 between each of the elongate recesses 130 and inner surface 75 of outer portion 102. Accordingly, in one aspect, each adjacent pair of protrusions 150 defines the side walls of each respective conduit 160. The conduits 160 extend a majority of a length (represented by L in FIG. 9) of the outer tubular member 18 to provide a fluid communication pathway from a proximal section 40 (at which fluid 58 is supplied from irrigation port 30 via proximal window 47 (FIG. 6) and via circular recess 140) to the distal section 44. In one aspect, a surface 141 of circular recess 140 (also seen in FIG. 10) and a bottom portion of each recess 130 have substantially the same elevation at junction 155 (between circular recess 150 and the respective recesses 130) to provide a generally seamless transition therebetween.

Accordingly, one or more conduits 160 shown in FIGS. 11-12 correspond to (and define just one configuration of) interior passage 64 of side wall 60 of outer tubular member 18 that was previously described in association with FIG. 5. Therefore, conduits 160 define a fluid flow pathway internally within side wall 60 of outer tubular member 18 to deliver fluid 58 (from fluid source 32) to bur 24 and target tissue 82 at treatment site 80. As previously noted, this delivered fluid will flood the treatment site 80 to cool the bur 24 during rotation and/or to lubricate the target tissue 82, thereby increasing the effectiveness of the debriding action of the bur 24.

Moreover, because the irrigation fluid pathway is contained internally within the sidewall 60 of the outer tubular member 18, the outer tubular member 18 has a smaller overall cross-sectional profile. In another aspect, the outer surface 74 of the outer tubular member 18 is generally uniform and generally smooth without significant protrusions, such as the protrusion(s) that would otherwise be formed by an irrigation tube externally attached to instrument as seen in conventional instruments. With this in mind, this smaller cross-sectional profile provides instrument 10 with greater maneuverability to enable distal section 44 of instrument 10 to pass through various soft tissues and bony structures with less likelihood of the instrument 10 catching on soft tissues and bony structures encountered along a path to a treatment site at which rotation of bur 24 is deployed.

Regardless of exact form, the micro-burring instrument 10 of the present disclosure is useful in performing various sinus operations and other procedures. By way of example, and with reference to the one embodiment of FIGS. 1 and 2, the assembled instrument 10 is deployed to the target site. For example, in a surgical procedure, the instrument 10 is maneuvered to the treatment site 80 and the bur 24 is positioned against the bone or other target tissue 82, as illustrated in FIG. 5. Other related surgical techniques may be performed before, during, or after application of instrument 10.

Next, the inner tubular member 22 is then rotated relative to the outer tubular member 18, such that the bur 24 burs (e.g., cuts or abrades) the contacted cartilage and/or bone. As best seen in FIG. 5, the bur 24, and thus the target site 82, are periodically or continuously flushed with an irrigation fluid via the interior passage 64 (for example, the irrigation conduits 160) extending within the side wall 60 of the outer tubular member 18.

In addition to the surgical procedure described above, the micro-burring instrument 10 of the present disclosure can be used to perform a variety of other surgical procedures in which hard tissue is debrided or cut while flooding the treatment site with fluid to irrigate the bur and the target tissue.

Nevertheless, it is understood that an alternative embodiment can be formed by modifying the embodiment of instrument 10 (FIGS. 1-12) to include an exteriorly extending aspiration passage proximal the bur 24 that is otherwise fluidly connected to the central lumen 147. This arrangement provides an externally-located aspiration mechanism in combination with the internally located irrigation mechanism formed in accordance with principles of the present disclosure and that was previously described in association with FIGS. 1-12.

As familiar to those skilled in the art, the outer tubular member 18 and the inner tubular member 22 are formed from biocompatible metallic materials, such as stainless steel, titanium alloys, and the like. Accordingly, at least the outer tubular member 18 defines a generally rigid member.

Although the present disclosure has been described with reference to preferred embodiments, workers skilled in the art will recognize that changes can be made in form and detail without departing from the spirit and scope of the present disclosure.

What is claimed is:

1. A surgical instrument comprising:
   an outer tubular member having a proximal section, a distal section, and a central lumen and defining an irrigation pathway;
   an inner tubular member rotatably received within the central lumen, a distal end of the inner tubular member forming a cutting member extending distally beyond, and exposed relative to, the distal section; wherein the irrigation pathway is not in fluid communication with the inner tubular member; and
   a bearing assembly positioned at the distal section of the outer tubular member and the inner tubular member so as to allow rotation of the inner tubular member relative to the outer tubular member about a central axis of the distal section, the bearing assembly contacting the cutting member to limit axial movement of the cutting member; wherein the bearing assembly is in fluid communication with the irrigation pathway.

2. The surgical instrument of claim 1, wherein the bearing assembly includes a plurality of balls positioned within a race in the inner tubular member.

3. The surgical instrument of claim 2, wherein the balls are exposed to the irrigation pathway.

4. The surgical instrument of claim 2, wherein the race is located within a proximal end of the cutting member.

5. The surgical instrument of claim 1, wherein the outer tubular member includes an inner portion and an outer portion, and further wherein the inner portion forms a plurality of recesses spaced about a circumference of the inner portion.

6. The surgical instrument of claim 5, wherein the bearing assembly further includes a plurality of balls each positioned within a race in the inner tubular member and within respective ones of the recesses.

7. The surgical instrument of claim 1, wherein the bearing assembly is arranged and configured to limit axial movement of the cutting member in a direction parallel to the central axis.

8. The surgical instrument of claim 1, wherein the outer tubular member defines a bend.

9. The surgical instrument of claim 8, wherein the inner tubular member comprises a flexible spring section configured to conform to the bend of the outer tubular member.

10. The surgical instrument of claim 8, wherein the bearing assembly is located distal to the bend.

11. The surgical instrument of claim 1, wherein the irrigation pathway is separate from the central lumen.

12. A surgical instrument comprising:
    an outer tubular member having a proximal section and a distal section, wherein the outer tubular member defines a central lumen and an irrigation pathway separate from the central lumen;
    an inner tubular member rotatably received within the central lumen, a distal end of the inner tubular member forming a cutting member extending distally beyond, and exposed relative to, the distal section; wherein the irrigation pathway is not in fluid communication with the inner tubular member; and
    a bearing assembly coupled to the distal section of the outer tubular member and the inner tubular member so as to allow rotation of the inner tubular member relative to the outer tubular member about a central axis of the distal section; wherein the bearing assembly is in fluid communication with the irrigation pathway.

13. The surgical instrument of claim 12, wherein the bearing assembly is arranged and configured to limit axial movement of the cutting member.

14. The surgical instrument of claim 12, wherein the bearing assembly includes a plurality of balls positioned within a race in the inner tubular member.

15. The surgical instrument of claim 14, wherein the race is located within a proximal end of the cutting member.

16. The surgical instrument of claim 14, wherein the balls are positioned within apertures formed in the outer tubular member, the apertures being open to the irrigation pathway.

17. The surgical instrument of claim 12, wherein the outer tubular member defines a bend.

18. The surgical instrument of claim 17, wherein the bearing assembly is distal to the bend.

19. The surgical instrument of claim 17, wherein the inner tubular member comprises a flexible spring section configured to conform to the bend of the outer tubular member.

20. The surgical instrument of claim 19, wherein the flexible spring section is positioned proximate the cutting member.

\* \* \* \* \*